(12) United States Patent
Feldkamp et al.

(10) Patent No.: US 10,813,798 B2
(45) Date of Patent: Oct. 27, 2020

(54) ABSORBENT COMPOSITE INCLUDING SWELLABLE ABSORBENT FIBERS

(71) Applicant: Kimberly-Clark Worldwide, Inc., Neenah, WI (US)

(72) Inventors: Joseph R. Feldkamp, Appleton, WI (US); Maria Del Carmen Lopez Garcia, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 428 days.

(21) Appl. No.: 15/742,307

(22) PCT Filed: Jun. 2, 2016

(86) PCT No.: PCT/US2016/035403
§ 371 (c)(1),
(2) Date: Jan. 5, 2018

(87) PCT Pub. No.: WO2017/019176
PCT Pub. Date: Feb. 2, 2017

(65) Prior Publication Data
US 2018/0193517 A1 Jul. 12, 2018

Related U.S. Application Data

(60) Provisional application No. 62/198,254, filed on Jul. 29, 2015.

(51) Int. Cl.
*A61F 13/53* (2006.01)
*A61L 15/60* (2006.01)
(Continued)

(52) U.S. Cl.
CPC .............. *A61F 13/53* (2013.01); *A61L 15/42* (2013.01); *A61L 15/60* (2013.01);
(Continued)

(58) Field of Classification Search
CPC ................ A61F 2013/530226–530248; A61F 2013/530299–530321;
(Continued)

(56) References Cited

U.S. PATENT DOCUMENTS 6,433,058 B1 * 8/2002 Weir .......................... C08J 3/12
523/105
6,696,618 B2 2/2004 Dodge, II
(Continued)

FOREIGN PATENT DOCUMENTS

EP 0339461 B1 1/1993
JP 3722569 B2 11/2005
(Continued)

*Primary Examiner* — Susan S Su
(74) *Attorney, Agent, or Firm* — Kimberly-Clark Worldwide, Inc.

(57) ABSTRACT

Generally, an absorbent composite comprising between about 20% and about 80% by weight of the particulate superabsorbent material and between about 20% and 80% by weight of a swellable absorbent fiber is disclosed herein. The swellable absorbent fiber is substantially water-insoluble and water-swellable and a centrifuge retention capacity of between 5 and 20 grams per gram after four hours and reaches at least 66% of centrifuge retention capacity between about 2 and about 50 seconds.

23 Claims, 6 Drawing Sheets

(51) Int. Cl.
*A61L 15/42* (2006.01)
*A61F 13/15* (2006.01)
*B01J 20/28* (2006.01)

(52) U.S. Cl.
CPC ........... *A61F 2013/15463* (2013.01); *A61F 2013/5307* (2013.01); *A61F 2013/530226* (2013.01); *A61F 2013/530481* (2013.01); *A61F 2013/530708* (2013.01); *B01J 20/28004* (2013.01); *B01J 20/28028* (2013.01)

(58) Field of Classification Search
CPC ............... A61F 2013/530379–53043; A61F 2013/530489; A61F 2013/530591; A61F 2013/530613; A61F 13/53; A61F 13/15203; A61F 2013/15463; A61F 2013/15471
See application file for complete search history.

(56) References Cited

U.S. PATENT DOCUMENTS

| | | | |
|---|---|---|---|
| 8,426,671 | B2 | 4/2013 | Steffen |
| 2004/0054342 | A1 | 3/2004 | Newbill |
| 2005/0090173 | A1 | 4/2005 | Weisman |
| 2006/0135932 | A1 | 6/2006 | Abuto |
| 2007/0093767 | A1* | 4/2007 | Carlucci .................. A61L 15/60 604/368 |
| 2008/0082064 | A1* | 4/2008 | Luo .......................... A61L 15/60 604/367 |
| 2008/0082069 | A1* | 4/2008 | Qin .......................... A61L 15/60 604/376 |
| 2008/0147026 | A1 | 6/2008 | Qin |
| 2009/0099541 | A1* | 4/2009 | Qin .......................... A61F 13/53 604/376 |
| 2011/0152813 | A1 | 6/2011 | Ellingson |
| 2013/0079741 | A1 | 3/2013 | Nakashita |
| 2014/0295135 | A1 | 10/2014 | Thompson, Jr. |
| 2015/0119837 | A1 | 4/2015 | Thompson, Jr. |
| 2015/0292117 | A1* | 10/2015 | Daniel ..................... A61L 15/24 604/372 |

FOREIGN PATENT DOCUMENTS

| | | |
|---|---|---|
| WO | 0142339 A1 | 6/2001 |
| WO | 07046052 A1 | 4/2007 |
| WO | 17171774 A1 | 10/2017 |
| WO | 17171777 A1 | 10/2017 |
| WO | 17171781 A1 | 10/2017 |
| WO | 17171782 A1 | 10/2017 |
| WO | 17171785 A1 | 10/2017 |
| WO | 18111292 A1 | 6/2018 |

* cited by examiner

ABSORBENT COMPOSITE INCLUDING SWELLABLE ABSORBENT FIBERS

BACKGROUND

Articles, such as absorbent articles, are useful for absorbing many types of fluids, including fluids secreted or eliminated by the human body. Such articles typically contain an absorbent core that can include superabsorbent materials in a fibrous matrix.

The inclusion of absorbent materials in a fibrous matrix and their incorporation into absorbent articles is known. The incorporation of superabsorbent materials into these products has had the effect of reducing the products' overall bulk while at the same time increasing its liquid absorbent capacity and enhancing skin dryness for the products' wearers.

Superabsorbent materials are generally polymer based and are available in many forms, such as powders, granules, microparticles and films, for example. Upon contact with fluids, such superabsorbents swell by absorbing the fluids into their structures. Superabsorbents are water-swellable, generally water-insoluble absorbent materials having a liquid absorbent capacity of at least about 10, preferably of about 20, and often up to about 100 times their weight in saline.

A variety of materials have been described for use as absorbent materials in absorbent articles. Included among these materials are natural-based materials such as agar, pectin, gums, carboxyalkyl starch and carboxyalkyl cellulose, such as carboxymethyl cellulose. Natural-based materials tend to form gels rather than maintaining a solid form and are therefore not favored in these products. Synthetic materials such as sodium salts of polyacrylates, polyacrylamides, and hydrolyzed polyacrylonitriles have also been used as absorbent materials in absorbent articles. Although natural-based absorbing materials are well known, these materials have not gained wide usage in absorbent articles because of their relatively inferior absorbent properties compared to synthetic absorbent materials, such as sodium polyacrylates. In contrast to the natural-based absorbents, synthetic absorbent materials are generally capable of absorbing large quantities of liquid while maintaining a relatively non-gelatinous form. Synthetic absorbent materials, often referred to as superabsorbent polymers (SAP), have been incorporated into absorbent articles to provide higher absorbency under pressure and higher absorbency per gram of absorbent material. Superabsorbent polymers are generally supplied as particles having a diameter in the range from about 20-800 microns.

In general, superabsorbent materials can quickly absorb fluids insulted into such articles (i.e., a high absorption rate), and have a high capacity which can lock-up fluids immediately. However, this fast absorption rate may also prevent fluid from being distributed to locations away from the fluid insulting point, often referred to as a target zone. This may cause the fluid insulting the target area to reach its capacity much earlier than other regions of the article, resulting in early leakage and low overall product absorbency efficiency.

Absorbent cores within incontinence products often resort to flat construction out of a need for manufacturing simplicity, cost saving and a desire for thinner products. This tends to challenge our ability to fulfill requirements for rapid liquid intake and good liquid distribution. Failure to meet either of those requirements will lead to leakage, poor wet fit or both. In addition, thin cores lead to inadequate intake rates and liquid spreading is so poor that cores become excessively thick in the crotch, producing poor wet-fit on consumers.

Thus, there is a need for an absorbent composite for use in absorbent articles which maintains overall high absorbency properties, but also effectively distributes fluid to regions outside the point of insult to improve overall absorbent efficiency of the article. There is also a need to develop an absorbent material which has a relatively low capacity and a significantly quick absorption rate to obtain these benefits. The present invention seeks to fulfill these needs and provides further related advantages.

SUMMARY

Generally, an absorbent composite comprising between about 20% and about 80% by weight of the particulate superabsorbent material and between about 20% and 80% by weight of a swellable absorbent fiber is disclosed herein. The swellable absorbent fiber is substantially water-insoluble and water-swellable and a centrifuge retention capacity of between 5 and 20 grams per gram after four hours and reaches at least 66% of centrifuge retention capacity between about 2 and about 50 seconds. Including swellable absorbent fibers with these properties within the absorbent composite increases fluid transfer and distribution within the composite leading to better intake and product fit.

DEFINITIONS

Figure 1:
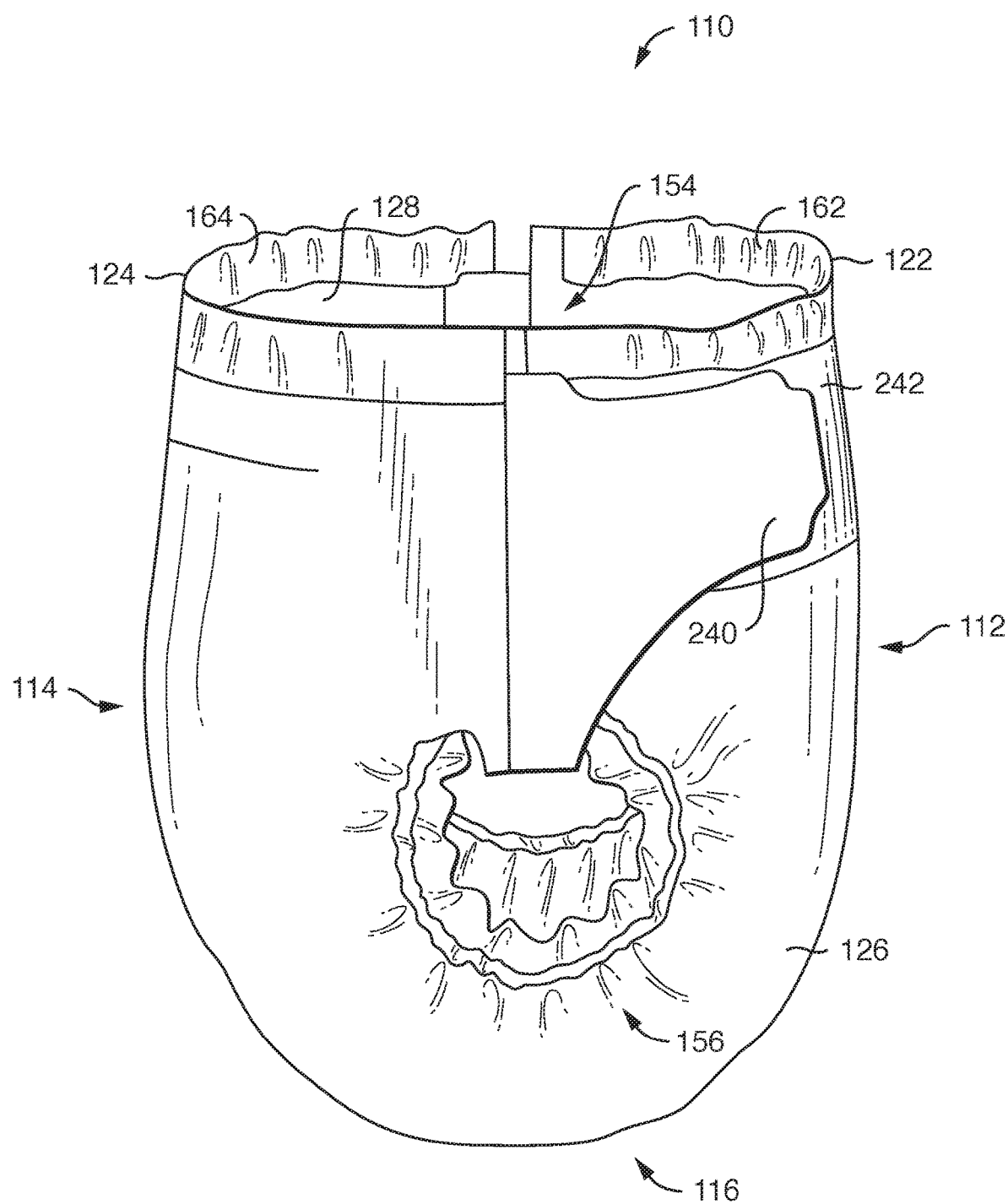
FIG. 1 is a side view illustration of an embodiment of an absorbent article.

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements.

The term "carded web" refers herein to a web containing natural or synthetic staple fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "g/cc" refers herein to grams per cubic centimeter.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a polymeric material which becomes pliable or moldable above a specific temperature and returns to a solid state upon cooling.

Centrifuge Retention Capacity (CRC) Test

The Centrifuge Retention Capacity (CRC) Test measures the ability of the absorbent sample to retain liquid therein after being saturated and subjected to centrifugation under controlled conditions. The resultant retention capacity is stated as grams of liquid retained per gram weight of the sample (g/g). For the fiber samples, the sample to be tested is used as is.

The retention capacity is measured by placing 0.2±0.005 grams of the sample into a water-permeable bag which will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat sealable filter paper, works well for most applications. The bag is formed by folding a 5-inch by 3-inch (12.7-cm by 7.6-cm) sample of the bag material in half and heat-sealing two of the open edges to form a 2.5-inch by 3-inch (6.4-cm by 7.6-cm) rectangular pouch. The heat seals should be about 0.25 inches (0.64 cm) inside the edge of the material. After the sample is placed in the pouch, the remaining open edge of the pouch is also heat-sealed. Empty bags are also made to serve as controls. Three samples (i.e., filled and sealed bags) are prepared for the test. The filled bags must be tested within three minutes of preparation unless immediately placed in a sealed container, in which case the filled bags must be tested within thirty minutes of preparation.

The bags are placed between two TEFLON coated fiberglass screens having 3 inch (7.6 cm) openings (available from Taconic Plastics, Inc., having a place of business in Petersburg, N.Y., U.S.A.) and submerged in a pan of the test solution at 23 degrees Celsius, making sure that the screens are held down until the bags are completely wetted. After wetting, the samples remain in the solution for about 20±1 minutes, at which time they are removed from the solution and centrifuged as described in the paragraph below. The samples after being centrifuged and weighed are placed in the solution again for the next measurement. The samples remain in the solution for about 40±1 minutes, at which time they are removed from the solution, centrifuged and weighed to measure their CRC values at 1 hour (20 minutes+ 40 minutes=60 minutes). The same samples are used for measuring their CRC values at 2 hours and 4 hours (additional soaking time of 1 hour and 2 hours respectively) in the same procedure. Other soaking time intervals may be used for fibers that are expected to exhibit faster absorption rates. For multiple tests, the pan should be emptied and refilled with fresh test solution after 24 bags have been saturated in the pan.

The wet bags taken from the testing solution at different measuring times are then placed into the basket of a suitable centrifuge capable of subjecting the samples to a g-force of about 350. One suitable centrifuge is a Heraeus LaboFuge 400 having a water collection basket, a digital rpm gauge, and a machined drainage basket adapted to hold and drain the bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the retention capacity is determined as:

$$CRC = \frac{\text{sample/bag wt after centrifuge} - \text{empty bag wt after centrifuge} - \text{dry sample wt}}{\text{dry sample wt}}$$

where "wt" in the above equation stands for weight.

The three samples are tested and the results are averaged to determine the centrifuge retention capacity (CRC). The samples are tested at 23±1° C. and at 50±2% relative humidity. Unless otherwise stated, all CRC values refer to the value after 4 hours of soaking time.

Absorption Time Constant for 66% Capacity Test

The absorption time constant of the swellable absorbent fiber is determined in the following manner: The CRC value after 4 hours of soaking time is multiplied by 66%. A graph of the CRC value as a function of time is then used to determine the time required for the material to swell to 66% of its 4 hour value. This is done by plotting the data for 0, 20 minutes, 1 hour, 2 hours, and 4, or other appropriate time intervals as discussed in the Centrifuge Retention Capacity Test above, hours using MICROSOFT OFFICE EXCEL spreadsheet program, using the standard graphing function with smoothed lines connecting data points, and interpolating the data as necessary, as would be obvious to one skilled in the art. The absorption time constant is the time (in seconds) required to swell to 66% of its 4 hour value.

Core Retention Capacity Test

The total absorbent capacity of the absorbent core may be determined by using the Retention Capacity Test Method. This test method measures the amount of fluid retained by an absorbent insert under external pressure. An initial weight of the absorbent insert is measured and then the absorbent insert is submerged in a 0.9% saline solution for 20 minutes. After the saturation time, 0.5 psi pressure is applied across the entire absorbent insert for 5 minutes and the excess saline solution is allowed to drain. After the pressure time, the weight of the saturated absorbent insert is measured. The total absorbent capacity is calculated as the saturated weight minus the initial weight.

DETAILED DESCRIPTION

Generally, an absorbent composite comprising between about 20% and about 80% by weight of the particulate superabsorbent material and between about 20% and 80% by weight of a swellable absorbent fiber is disclosed herein. The swellable absorbent fiber is substantially water-insoluble and water-swellable and a centrifuge retention capacity of between 5 and 20 grams per gram after four hours and reaches at least 66% of centrifuge retention capacity between about 2 and about 50 seconds.

Including swellable absorbent fibers within the absorbent composite increases fluid transfer and distribution within the composite leading to better intake and product fit. The swellable absorbent fibers provide this benefit in two ways. First, increased diameter (as a result of rapid swelling) leads to increased permeability (or hydraulic conductivity) since permeability is inversely proportional to the square of surface area per unit volume of solid. For example, if diameter increases two-fold, permeability is expected to increase by four times since surface area per unit volume of solid has decreased by four times. The benefit of increased permeability in the intake region is more rapid liquid transport out of the intake region. Second, increased diameter leads to a lower capillary pressure since capillary pressure is typically linearly proportional to surface area per unit volume of solid. A lower capillary pressure in the intake region, combined with high capillary pressure in more remote regions of the absorbent core, provides a more effective driving force to aid the transport of liquid out of the intake zone toward more remote regions of the core.

To deliver the proposed benefits to both permeability and capillary pressure as described, fiber swelling needs to take place on a time frame that matches typical intake times, ranging from about 5 to 15 seconds. Short swelling times are only expected to occur when swelling absorbent fiber diameters are small, ranging from about 10 microns to 50 microns, and then don't swell too much thereafter. Though not obvious, complete replacement of conventional particulate superabsorbent materials with swelling absorbent fibers is not preferred. If particulate superabsorbent material was completely replaced with the proposed small diameter swelling absorbent fiber, permeability would be driven downward excessively, to the point of hindering both adequate liquid spreading and liquid intake. Rather, there is an optimal amount of swelling absorbent fiber to be used in replacement of conventional particular superabsorbent particles. For purposes herein, a fiber is a material has a largest dimension and smallest dimension, wherein the ratio of largest dimension to smallest dimension is at least 10:1. For example, if a fiber has a width of 50 microns, it has a length of at least 500 microns. Materials that have a smaller ratio are considered particulate materials.

Therefore, the absorbent composite desirably includes between about 20% and about 80% by weight of the particulate superabsorbent material and between about 20% and 80% by weight of a swellable absorbent fiber. In desirable embodiments, the absorbent composite includes at least about 45% by weight of the swellable absorbent fibers. More desirably, the absorbent core comprises between 45% and 65% by weight of the swelling absorbent fibers.

As described above, absorbent fiber swelling needs to take place on a time frame that matches typical intake times. Desirably, the swellable absorbent fiber reaches at least 66% of the centrifuge retention capacity in between about 2 and about 50 seconds. Even more desirably, the swellable absorbent fiber reaches at least 66% of the centrifuge retention capacity in between about 2 and about 20 seconds. Swelling absorbent fibers exhibiting this speed of absorption enable better fluid distribution within the composite.

In various embodiments, the swelling absorbent fiber has a fiber diameter of between 10 and 50 microns. A swelling absorbent fiber with this small diameter has a higher surface area to fiber volume ratio allowing for the speed of absorption required to better handle liquid distribution within the composite.

The swellable absorbent fiber may be any fiber known to one skilled in the art that exhibits the swelling times, diameters and capacity as described herein. Examples of suitable swellable absorbent fibers include, superabsorbent fibers, natural fibers; cellulosic fibers; crosslinked cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been modified by suitable means to result in the swelling times, diameters and capacity parameters described herein.

Sodium polyacrylate is one example of an acceptable chemistry, whereby swelling is promoted from the osmotic activity of sodium ions that counter charge on the polyacrylate backbone. The proportion of ionization of the polyacrylate can be adjusted to alter capacity so that capacity falls into the desired range. Also, cross-linking can be adjusted in order to obtain a more desired capacity. Other methods can be used as well, such as ion exchange of sodium with divalent ions that inhibit excessive swelling.

As described above, the absorbent composite also includes a particulate superabsorbent material. Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Typically, a superabsorbent material can be capable of absorbing at least about ten times its weight of an aqueous liquid. In an embodiment, the superabsorbent material can absorb more than twenty-four times its weight in liquid. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Conglomerates of particles of superabsorbent materials may also be used in the absorbent composite. Other examples would include cellulosic fibers which have been functionalized with either anionic or cationic moieties, such as carboxylate or amino groups or a combination of the two types of groups.

In an embodiment, the absorbent composite can have at least about 35% by weight of a superabsorbent material. In an embodiment, the absorbent composite can have at least about 35 to about 55% by weight of a superabsorbent material. Examples of superabsorbent material include, but are not limited to, FAVOR SXM-9500 or equivalent available from Evonik Industries, Greensboro, N.C., U.S.A. and HYSORB 8760 or equivalent available from BASF Corporation, Charlotte, N.C., U.S.A.

Optimal concentrations within the composite for exemplary superabsorbent material and swellable absorbent fibers described herein have been discovered. Noting that peak, or maximum, liquid density should decrease if spreading has been more effective, a composite having a superabsorbent material weight percentage of about 45% exhibits the least amount of peak liquid density. For the distance between liquid fronts (a front being defined as the location where liquid density has fallen to 66% of maximum) a composite having a superabsorbent material weight percentage of about 40% exhibits the largest spreading distance. The total Core Retention Capacity of the composite described herein may be between about 200 g and 990 g of 0.9% saline.

In an embodiment, the absorbent composite may be constructed of a single layer of materials, or in the alternative, may be constructed of two layers of materials or more. In one embodiment, the absorbent composite may be homogenous matrix of the swellable absorbent fiber and the particulate superabsorbent material. In an embodiment in which the absorbent composite has two layers, the absorbent composite can have a wearer facing layer suitably composed of hydrophilic fibers and a garment facing layer suitably composed at least in part of a high absorbency material commonly known as superabsorbent material. In such an embodiment, the wearer facing layer of the absorbent composite can be suitably composed of cellulosic fluff, such as wood pulp fluff, and the garment facing layer of the absorbent composite can be suitably composed of superabsorbent material, or a mixture of cellulosic fluff and superabsorbent material. As a result, the wearer facing layer can have a lower absorbent capacity per unit weight than the garment facing layer. The wearer facing layer may alternatively be composed of a mixture of hydrophilic fibers and superabsorbent material. It is also contemplated that the garment facing layer may be composed solely of superabsorbent material without departing from the scope of this disclosure. It is also contemplated that, in an embodiment, each of the layers, the wearer facing and garment facing layers, can have a superabsorbent material such that the absorbent capacities of the two superabsorbent materials can be different and can provide the absorbent composite with a different absorbent capacity in the wearer facing layer than in the garment facing layer.

After formation of the absorbent composite, the absorbent composite described herein may be incorporated into an absorbent article. Various methods for constructing an absorbent article are described in U.S. patent application Ser. No. 14/062,278 filed Oct. 24, 2013 by Ruman et al.; U.S. patent application Ser. No. 14/068,918 filed Oct. 31, 2013 by Sina et al.; U.S. patent application Ser. No. 14/068,913 filed Oct. 31, 2013 by Bennett et al.; PCT Patent Application WO 00/37009 published Jun. 29, 2000 by A. Fletcher et al; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al., which are incorporated herein by reference.

Referring to FIG. 1, a disposable absorbent article 110 of the present disclosure is exemplified in the form of a diaper. It is to be understood that the present disclosure is suitable for use with various other personal care absorbent articles, such as, for example, feminine hygiene products, adult incontinence products and pads, without departing from the scope of the present disclosure. While the embodiments and illustrations described herein may generally apply to absorbent articles manufactured in the product longitudinal direction, which is hereinafter called the machine direction manufacturing of a product, it should be noted that one of ordinary skill could apply the information herein to absorbent articles manufactured in the latitudinal direction of the product which hereinafter is called the cross direction manufacturing of a product without departing from the spirit and scope of the disclosure. The absorbent article 110 illustrated in FIG. 1 includes a front waist region 112, a back waist region 114, and a crotch region 116 interconnecting the front and back waist regions, 112 and 114, respectively. The absorbent article 110 has a pair of longitudinal side edges, 118 and 120 (shown in FIG. 2), and a pair of opposite waist edges, respectively designated front waist edge 122 and back waist edge 124. The front waist region 112 can be contiguous with the front waist edge 122 and the back waist region 114 can be contiguous with the back waist edge 124.

Figure 2:
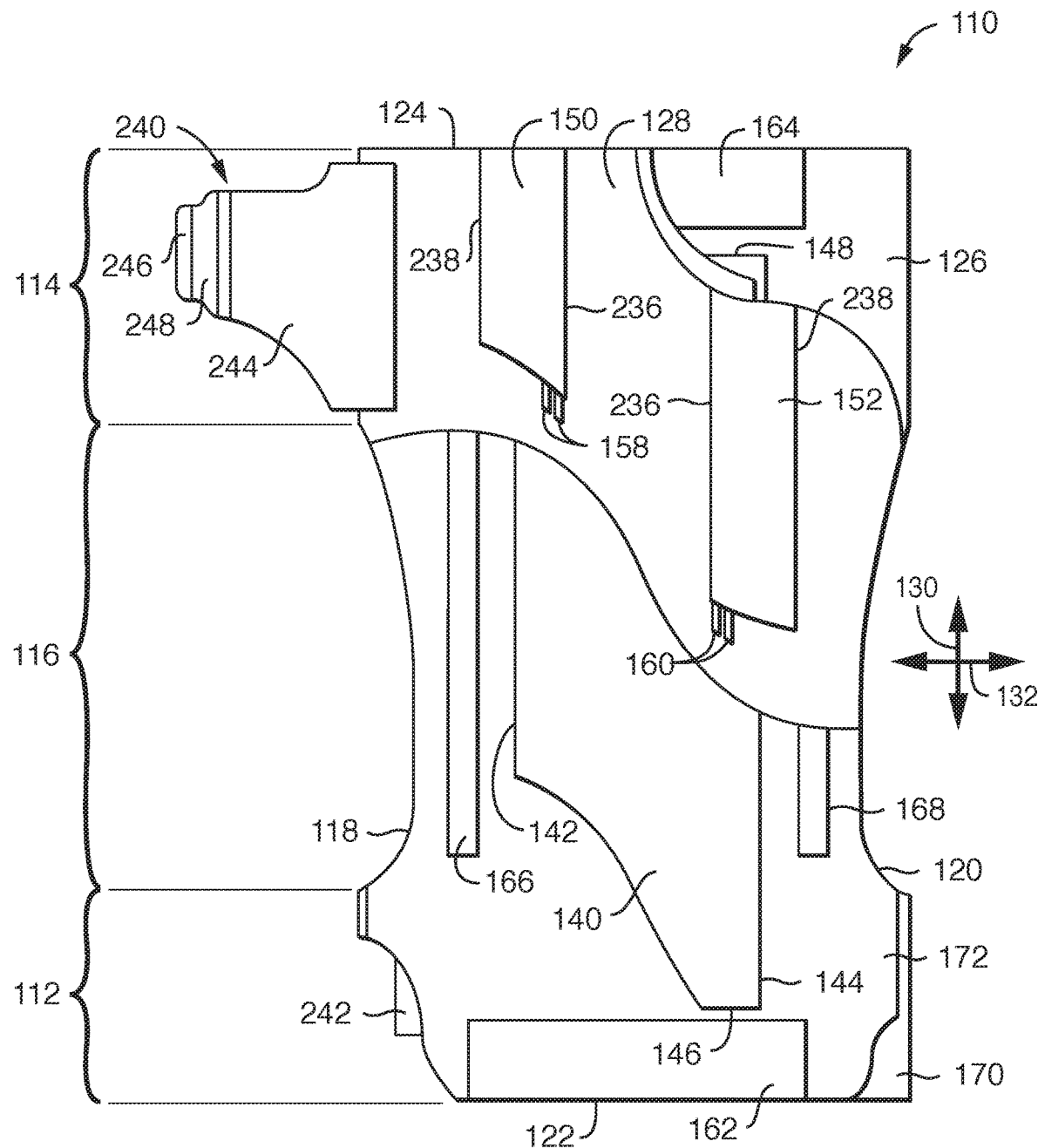
FIG. 2 is a top down view of an embodiment of an absorbent article with portions cut away for clarity.
Figure 3:
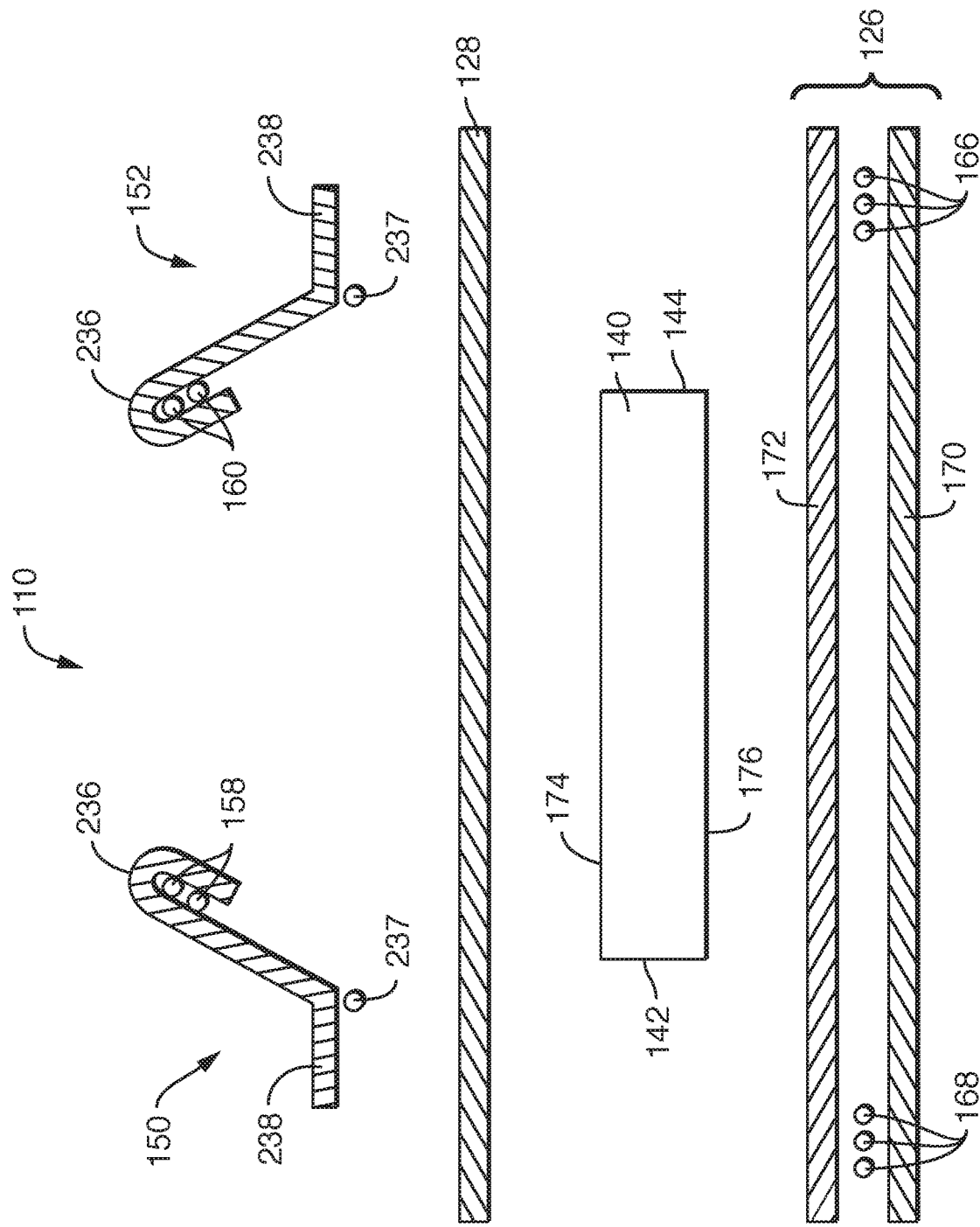
FIG. 3 is an exploded cross-sectional view of an embodiment of an absorbent article.

Referring to FIG. 2, a non-limiting illustration of an absorbent article 110, such as, for example, a diaper, is illustrated in a top down view with portions cut away for clarity of illustration. The absorbent article 110 can include an outer cover 126 and a body facing material 128. In an embodiment, the body facing material 128 can be bonded to the outer cover 126 in a superposed relation by any suitable means such as, but not limited to, adhesives, ultrasonic bonds, thermal bonds, pressure bonds, or other conventional techniques. The outer cover 126 can define a length, or longitudinal direction 130, and a width, or lateral direction 132, which, in the illustrated embodiment, can coincide with the length and width of the absorbent article 110. The longitudinal direction 130 and the lateral direction 132 of the absorbent article 110, and of the materials which form the absorbent article 110, can provide the X-Y planes, respectively, of the absorbent article 110 and of the materials which form the absorbent article 110. The absorbent article 110, and the materials which form the absorbent article 110, can also have a Z-direction. A measurement, taken under pressure, in the Z-direction of a material which forms the absorbent article 110 can provide a measurement of the thickness of the material. A measurement, taken under pressure, in the Z-direction of the absorbent article 110 can provide a measurement of the bulk of the absorbent article 110.

Referring to FIGS. 1-6, an absorbent composite 140 can be disposed between the outer cover 126 and the body facing material 128. The absorbent composite 140 can have longitudinal edges, 142 and 144, which, in an embodiment, can form portions of the longitudinal side edges, 118 and 120, respectively, of the absorbent article 110 and can have opposite end edges, 146 and 148, which, in an embodiment, can form portions of the waist edges, 122 and 124, respectively, of the absorbent article 110. In an embodiment, the absorbent composite 140 can have a length and width that are the same as or less than the length and width of the absorbent article 110. In an embodiment, a pair of containment flaps, 150 and 152, can be present and can inhibit the lateral flow of body exudates.

The front waist region 112 can include the portion of the absorbent article 110 that, when worn, is positioned at least in part on the front of the wearer while the back waist region 114 can include the portion of the absorbent article 110 that, when worn, is positioned at least in part on the back of the wearer. The crotch region 116 of the absorbent article 110 can include the portion of the absorbent article 110, that, when worn, is positioned between the legs of the wearer and can partially cover the lower torso of the wearer. The waist edges, 122 and 124, of the absorbent article 110 are configured to encircle the waist of the wearer and together define the central waist opening 154 (such as shown in FIG. 1). Portions of the longitudinal side edges, 118 and 120, in the crotch region 116 can generally define leg openings 156 (such as shown in FIG. 1) when the absorbent article 110 is worn.

The absorbent article 110 can be configured to contain and/or absorb liquid, solid, and semi-solid body exudates discharged from the wearer. For example, containment flaps, 150 and 152, can be configured to provide a barrier to the lateral flow of body exudates. A flap elastic member, 158 and 160, can be operatively joined to each containment flap, 150 and 152, in any suitable manner known in the art. The elasticized containment flaps, 150 and 152, can define a partially unattached edge that can assume an upright configuration in at least the crotch region 116 of the absorbent article 110 to form a seal against the wearer's body. The containment flaps, 150 and 152, can be located along the absorbent article 110 longitudinal side edges, 118 and 120, and can extend longitudinally along the entire length of absorbent article 110 or can extend partially along the length of the absorbent article 110. Suitable construction and arrangements for containment flaps, 150 and 152, are generally well known to those skilled in the art and are described in U.S. Pat. No. 4,704,116 issued Nov. 3, 1987, to Enloe and U.S. Pat. No. 5,562,650 issued Oct. 8, 1996 to Everett et al., which are incorporated herein by reference.

To further enhance containment and/or absorption of body exudates, the absorbent article 110 can suitably include a front waist elastic member 162, a rear waist elastic member 164, and leg elastic members, 166 and 168, as are known to those skilled in the art. The waist elastic members, 162 and 164, can be attached to the outer cover 126, the body facing material 128 along the opposite waist edges, 122 and 124, and can extend over part or all of the waist edges, 122 and 124. The leg elastic members, 166 and 168, can be attached to the outer cover 126, the body facing material 128 along the opposite longitudinal side edges, 118 and 120, and positioned in the crotch region 116 of the absorbent article 110.

Additional details regarding each of these elements of the absorbent article 110 described herein can be found below and with reference to the Figures.

Outer Cover:

The outer cover 126 can be breathable and/or liquid impermeable. The outer cover 126 can be elastic, stretchable or non-stretchable. The outer cover 126 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 126 can be constructed of a microporous polymeric film, such as polyethylene or polypropylene.

In an embodiment, the outer cover 126 can be a single layer of a liquid impermeable material. In an embodiment, the outer cover 126 can be suitably stretchable, and more suitably elastic, in at least the lateral or circumferential direction 132 of the absorbent article 110. In an embodiment, the outer cover 126 can be stretchable, and more suitably elastic, in both the lateral 132 and the longitudinal 130 directions. In an embodiment, the outer cover 126 can be a multi-layered laminate in which at least one of the layers is liquid impermeable. In an embodiment such as illustrated in FIGS. 3-6, the outer cover 126 may be a two layer construction, including an outer layer 170 material and an inner layer 172 material which can be bonded together such as by a laminate adhesive. Suitable laminate adhesives can be applied continuously or intermittently as beads, a spray, parallel swirls, or the like. Suitable adhesives can be obtained from Bostik Findlay Adhesives, Inc. of Wauwatosa, Wis., U.S.A. It is to be understood that the inner layer 172 can be bonded to the outer layer 170 utilizing ultrasonic bonds, thermal bonds, pressure bonds, or the like.

The outer layer 170 of the outer cover 126 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer 170 of an outer cover 126 can be a 20 gsm spunbond polypropylene non-woven web.

The liquid impermeable inner layer 172 of the outer cover 126 (or the liquid impermeable outer cover 126 where the outer cover 126 is of a single-layer construction) can be either vapor permeable (i.e., "breathable") or vapor impermeable. The liquid impermeable inner layer 172 (or the liquid impermeable outer cover 126 where the outer cover 126 is of a single-layer construction) may be manufactured from a thin plastic film, although other liquid impermeable materials may also be used. The liquid impermeable inner layer 172 (or the liquid impermeable outer cover 126 where the outer cover 126 is of a single-layer construction) can inhibit liquid body exudates from leaking out of the absorbent article 110 and wetting articles, such as bed sheets and clothing, as well as the wearer and caregiver. An example of a material for a liquid impermeable inner layer 172 (or the liquid impermeable outer cover 126 where the outer cover 126 is of a single-layer construction) can be a printed 19 gsm Berry Plastics XP-8695H film or equivalent commercially available from Berry Plastics Corporation, Evansville, Ind., U.S.A.

Where the outer cover 126 is of a single layer construction, it can be embossed and/or matte finished to provide a more cloth-like texture or appearance. The outer cover 126 can permit vapors to escape from the absorbent article 110 while preventing liquids from passing through. A suitable liquid impermeable, vapor permeable material can be composed of a microporous polymer film or a non-woven material which has been coated or otherwise treated to impart a desired level of liquid impermeability.

Absorbent Composite:

The absorbent 140 can be superposed over the inner layer 172 of the outer cover 126, extending laterally between the leg elastic members, 166 and 168, and can be bonded to the inner layer 172 of the outer cover 126, such as by being bonded thereto with adhesive. However, it is to be understood that the absorbent composite 140 may be in contact with, and not bonded with, the outer cover 126 and remain within the scope of this disclosure. In an embodiment, the outer cover 126 can be composed of a single layer and the absorbent composite 140 can be in contact with the single layer of the outer cover 126. In an embodiment, a layer, such as but not limited to, a core wrap layer 178, can be positioned between the absorbent composite 140 and the outer cover 126.

Figure 4:
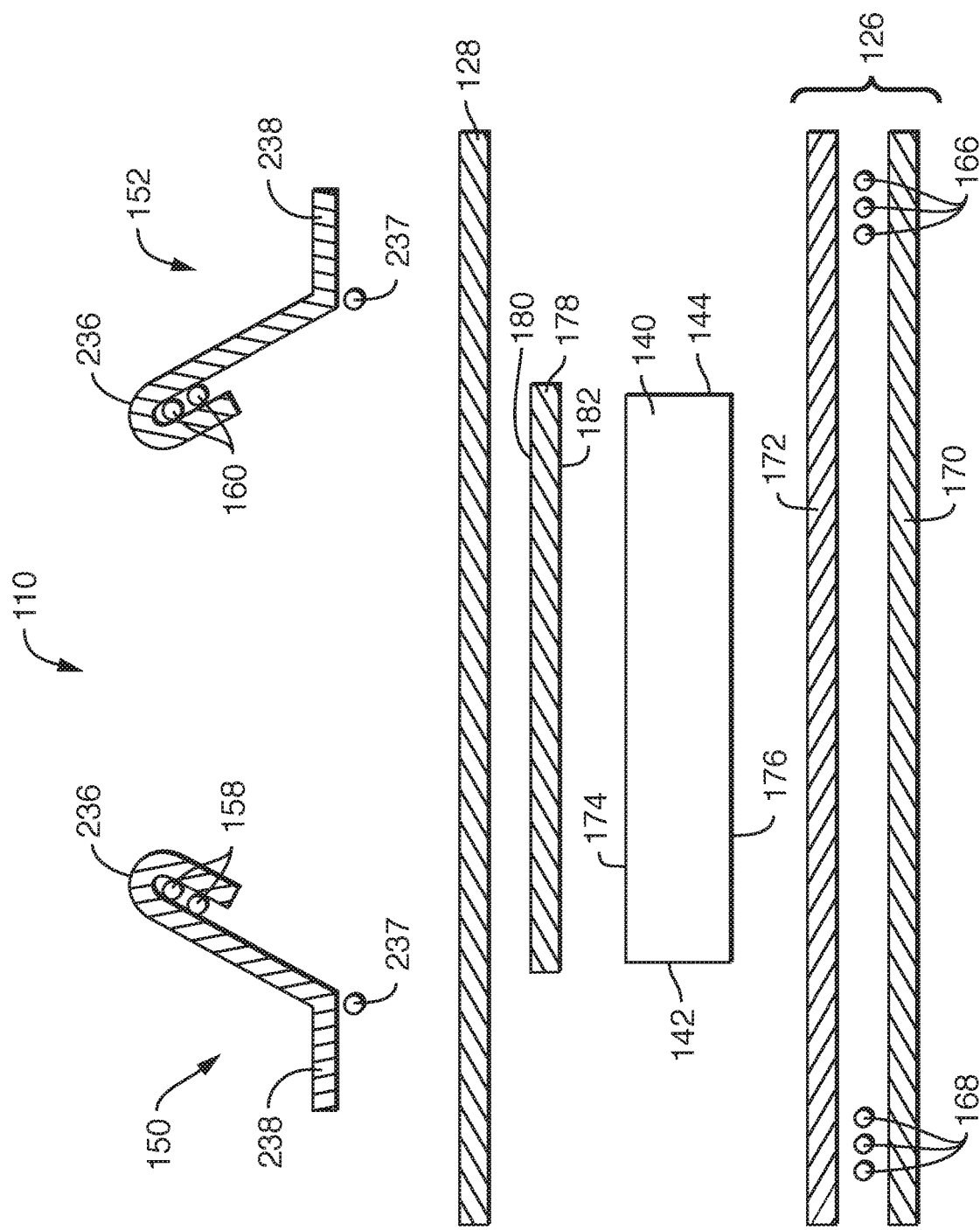
FIG. 4 is an exploded cross-sectional view of another embodiment of an absorbent article.

Core Wrap Layer:

In various embodiments, such as illustrated in the non-limiting example of FIG. 4, an absorbent article 110 can be constructed without a core wrap layer 178. In various embodiments, such as illustrated in the non-limiting examples of FIGS. 4-6, the absorbent article 110 can have a core wrap layer 178. The core wrap layer 178 can have a wearer facing surface 180 and a garment facing surface 182. In an embodiment, the core wrap layer 178 can be in contact with the absorbent composite 140. In an embodiment, the core wrap layer 178 can be bonded to the absorbent composite 140. Bonding of the core wrap layer 178 to the absorbent composite 140 can occur via any means known to one of ordinary skill, such as, but not limited to, adhesives. In an embodiment, such as illustrated in the non-limiting example of FIG. 5, a core wrap layer 178 can be positioned between the body facing material 128 and the absorbent core 140. In an embodiment, such as illustrated in the non-limiting example of FIG. 5, a core wrap layer 178 can completely encompass the absorbent composite 140 and can be sealed to itself. In such an embodiment, the core wrap layer 178 may be folded over on itself and then sealed using, for example, heat, adhesive and/or pressure. In an embodiment, such as, for example, in the non-limiting illustration of FIG. 6, a core wrap layer 178 may be composed of separate sheets of material which can be utilized to partially or fully encompass the absorbent composite 140 and which can be sealed together using a sealing means such as an ultrasonic bonder or other thermochemical bonding means or the use of an adhesive.

In an embodiment, the core wrap layer 178 can be in contact with and/or bonded with the wearer facing surface 174 of the absorbent composite 140. In an embodiment, the core wrap layer 178 can be in contact with and/or bonded with the wearer facing surface 174 and at least one of the edges, 142, 144, 146 and/or 148, of the absorbent composite 140. In an embodiment, the core wrap layer 178 can be in contact with and/or bonded with the wearer facing surface 174, at least one of the edges, 142, 144, 146 and/or 148, and the garment facing surface 176 of the absorbent composite 140. In an embodiment, the absorbent composite 140 may be partially or completely encompassed by a core wrap layer 178.

The core wrap layer 178 can be pliable, less hydrophilic than the absorbent composite 140, and sufficiently porous to thereby permit liquid body exudates to penetrate through the core wrap layer 178 to reach the absorbent composite 140.

In an embodiment, the core wrap layer 178 can have sufficient structural integrity to withstand wetting thereof and of the absorbent composite. In an embodiment, the core wrap layer 178 can be constructed from a single layer of material or it may be a laminate constructed from two or more layers of material.

In an embodiment, the core wrap layer 178 can include, but is not limited to, natural and synthetic fibers such as, but not limited to, polyester, polypropylene, acetate, nylon, polymeric materials, cellulosic materials such as wood pulp, cotton, rayon, viscose, LYOCELL® such as from Lenzing Company of Austria, or mixtures of these or other cellulosic fibers, and combinations thereof. Natural fibers can include, but are not limited to, wool, cotton, flax, hemp, and wood pulp.

In various embodiments, the core wrap layer selected from metlblown-spunbond-meltblown fabric, spunbond fabric, meltblown fabric, coform fabric, carded web, bonded-carded web, bicomponent spunbond fabric, spunlace, tissue, and combinations thereof.

In various embodiments, the core wrap layer 178 can include cellulosic material. In various embodiments, the core wrap layer 178 can be creped wadding or a high-strength tissue. In various embodiments, the core wrap layer 178 can include polymeric material. In an embodiment, a core wrap layer 178 can include a spunbond material. In an embodiment, a core wrap layer 178 can include a meltblown material. In an embodiment, the core wrap layer 178 can be a laminate of a meltblown nonwoven material having fine fibers laminated to at least one spunbond nonwoven material layer having coarse fibers. In such an embodiment, the core wrap layer 178 can be a spunbond-meltblown ("SM") material. In an embodiment, the core wrap layer 178 can be a spunbond-meltblown-spunbond ("SMS") material. A non-limiting example of such a core wrap layer 178 can be a 10 gsm spunbond-meltblown-spunbond material. In various embodiments, the core wrap layer 178 can be composed of at least one material which has been hydraulically entangled into a nonwoven substrate. In various embodiments, the core wrap layer 178 can be composed of at least two materials which have been hydraulically entangled into a nonwoven substrate. In various embodiments, the core wrap layer 178 can have at least three materials which have been hydraulically entangled into a nonwoven substrate. A non-limiting example of a core wrap layer 78 can be a 33 gsm hydraulically entangled substrate. In such an example, the core wrap layer 178 can be a 33 gsm hydraulically entangled substrate composed of a 12 gsm spunbond material, a 10 gsm wood pulp material having a length from about 0.6 cm to about 5.5 cm, and an 11 gsm polyester staple fiber material. To manufacture the core wrap layer 178 just described, the 12 gsm spunbond material can provide a base layer while the 10 gsm wood pulp material and the 11 gsm polyester staple fiber material can be homogeneously mixed together and deposited onto the spunbond material and then hydraulically entangled with the spunbond material.

In various embodiments, a wet strength agent can be included in the core wrap layer 178. A non-limiting example of a wet strength agent can be Kymene 6500 (557LK) or equivalent available from Ashland Inc. of Ashland, Ky., U.S.A. In various embodiments, a surfactant can be included in the core wrap layer 178. In various embodiments, the core wrap layer 178 can be hydrophilic. In various embodiments, the core wrap layer 178 can be hydrophobic and can be treated in any manner known in the art to be made hydrophilic.

In an embodiment, the core wrap layer 78 can be in contact with and/or bonded with an absorbent composite which is made at least partially of particulate material such as superabsorbent material. In an embodiment in which the core wrap layer 178 at least partially or completely encompasses the absorbent composite 140.

In an embodiment, the core wrap layer 178 may have a longitudinal length the same as, greater than, or less than the longitudinal length of the absorbent composite 140. The core wrap layer 178 can have a longitudinal length ranging from about 150 to about 520 mm.

Figure 5:
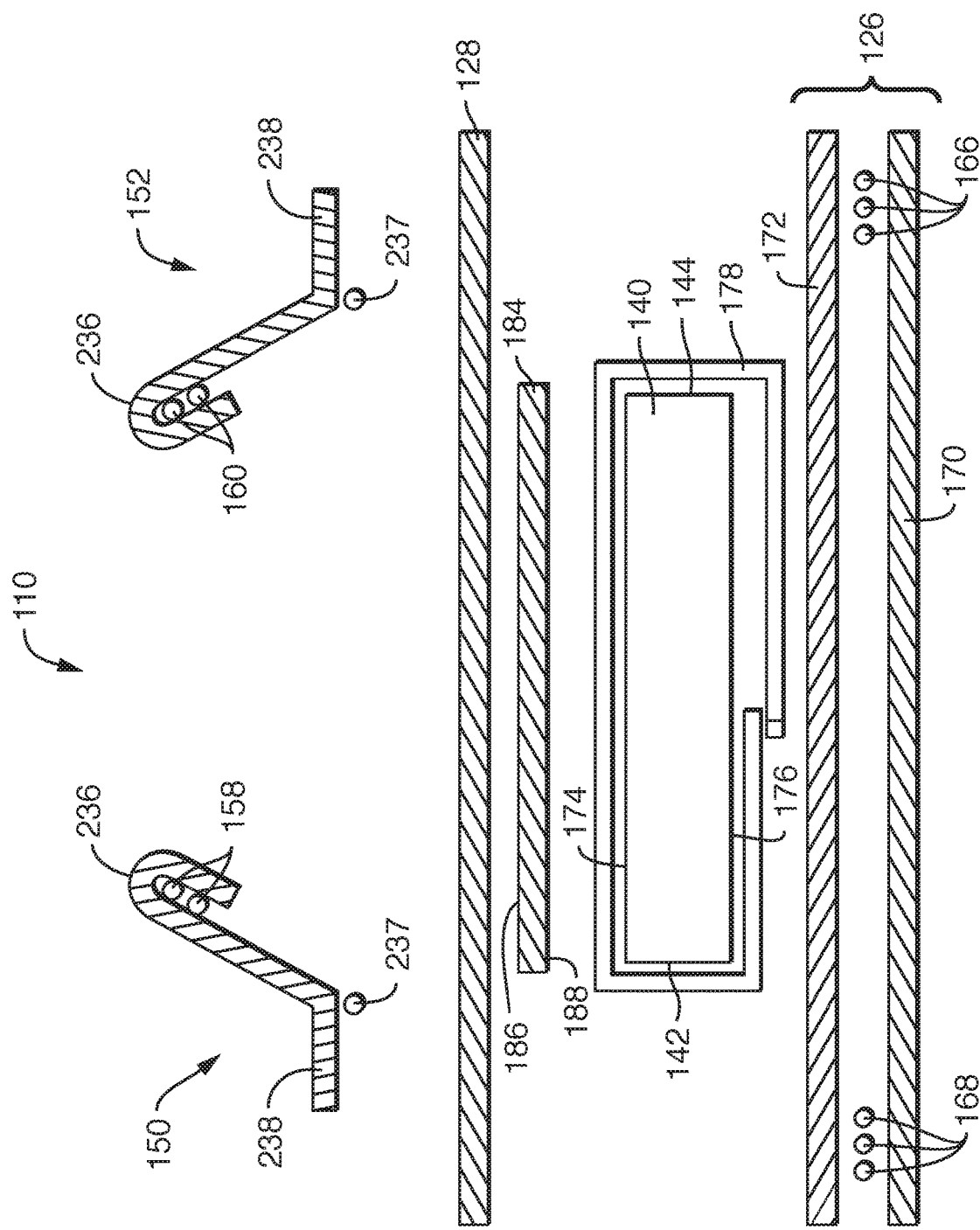
FIG. 5 is an exploded cross-sectional view of another embodiment of an absorbent article.
Figure 6:
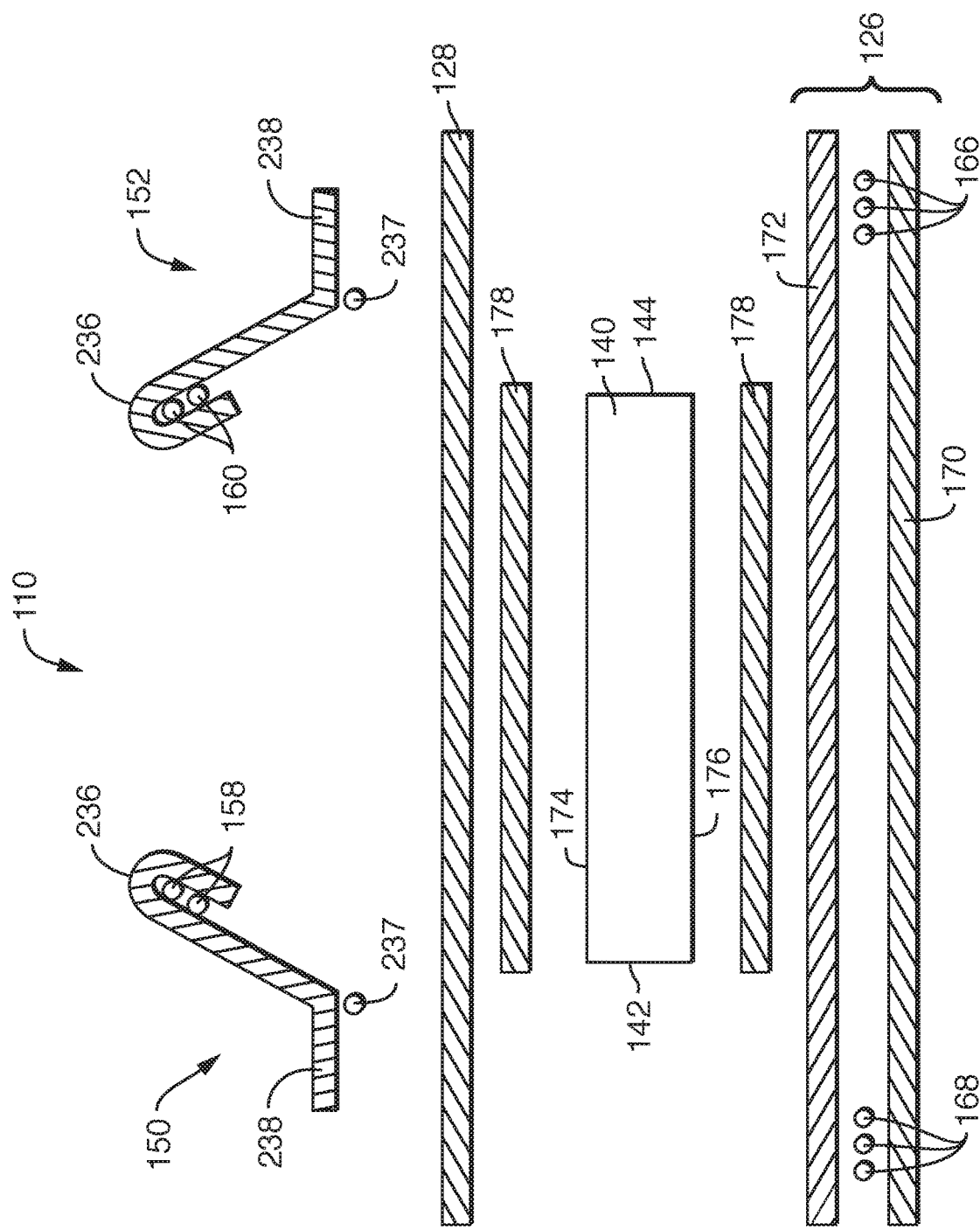
FIG. 6 is an exploded cross-sectional view of another embodiment of an absorbent article.

Acquisition Layer:

In various embodiments, such as illustrated, for example, in FIG. 5, the absorbent article 10 can have an acquisition layer 184. The acquisition layer 184 can help decelerate and diffuse surges or gushes of liquid body exudates penetrating the body facing material 128. In an embodiment, the acquisition layer 184 can be positioned between the body facing material 128 and the absorbent composite 140 to take in and distribute body exudates for absorption by the absorbent composite 140. In an embodiment, the acquisition layer 184 can be positioned between the body facing material 128 and a core wrap layer 178 if a core wrap layer 178 is present.

The acquisition layer 184 can have a wearer facing surface 186 and a garment facing surface 188. In an embodiment, the acquisition layer 184 can be in contact with and/or bonded with the body facing material 128. In an embodiment in which the acquisition layer 84 is bonded with the body facing material 128, bonding of the acquisition layer 184 to the body facing material 128 can occur through the use of an adhesive and/or point fusion bonding. The point fusion bonding can be selected from, but is not limited to, ultrasonic bonding, pressure bonding, thermal bonding, and combinations thereof. In an embodiment, the point fusion bonding can be provided in any pattern as deemed suitable.

The acquisition layer 184 may have any longitudinal length dimension as deemed suitable. In an embodiment, the acquisition layer 184 can have any length such that the acquisition layer 184 can be coterminous with the waist edges, 122 and 124, of the absorbent article 110.

In an embodiment, the longitudinal length of the acquisition layer 184 can be the same as the longitudinal length of the absorbent composite 140. In such an embodiment the midpoint of the longitudinal length of the acquisition layer 184 can substantially align with the midpoint of the longitudinal length of the absorbent composite 140.

In an embodiment, the longitudinal length of the acquisition layer 184 can be shorter than the longitudinal length of the absorbent composite 140. In such an embodiment, the acquisition layer 184 may be positioned at any desired location along the longitudinal length of the absorbent composite 140. As an example of such an embodiment, the absorbent article 110 may contain a target area where repeated liquid surges typically occur in the absorbent article 110. The particular location of a target area can vary depending on the age and gender of the wearer of the absorbent article 110 and design of the absorbent article 110. For example, males tend to urinate further toward the front region of the absorbent article 110 and the target area may be phased forward within the absorbent article 110. For example, the target area for a male wearer may be positioned about 70 mm forward of the longitudinal midpoint of the absorbent composite. The female target area can be located closer to the center of the crotch region 116 of the absorbent article 110. For example, the target area for a female wearer may be positioned about 26 mm forward of the longitudinal midpoint of the absorbent composite 140. As a result, the relative longitudinal placement of the acquisition layer 184 within the absorbent article 110 can be selected to best correspond with the target area of either or both categories of wearers.

In an embodiment, the acquisition layer 184 can have a size dimension that is the same size dimension as the target area of the absorbent article 110 or a size dimension greater than the size dimension of the target area of the absorbent article 110. In an embodiment, the acquisition layer 184 can be in contact with and/or bonded with the body facing material 28 at least partially in the target area of the absorbent article 110.

In various embodiments, the acquisition layer 184 can have a longitudinal length shorter than, the same as or longer than the longitudinal length of the absorbent composite 140. In an embodiment in which the absorbent article 110 is a diaper, the acquisition layer 184 may have a longitudinal length from about 120 to about 320 mm. In such an embodiment, the acquisition layer 184 may be shorter in longitudinal length than the longitudinal length of the absorbent composite 140 and may be phased from the front end edge 146 of the absorbent composite 140 a distance of from about 15 mm to about 40 mm. In an embodiment in which the absorbent article 110 may be a training pant or youth pant, the acquisition layer 184 may have a longitudinal length from about 120 to about 520 mm. In such an embodiment, the acquisition layer 184 may have a longitudinal length shorter than the longitudinal length of the absorbent composite 140 and may be phased a distance of from about 25 mm to about 85 mm from the front end edge 46 of the absorbent composite 40. In an embodiment in which the absorbent article 110 is an adult incontinence garment, the acquisition layer 184 may have a longitudinal length from about 200 mm to about 450 mm. In such an embodiment, the acquisition layer 184 may have a longitudinal length shorter than the longitudinal length of the absorbent composite 140 and the acquisition layer 184 may be phased a distance of from about 20 mm to about 75 mm from the front end edge 146 of the absorbent composite 140.

The acquisition layer 184 may have any width as desired. The acquisition layer 184 may have a width dimension from about 15 mm to about 180 mm. The width of the acquisition layer 184 may vary dependent upon the size and shape of the absorbent article 110 within which the acquisition layer 184 will be placed. The acquisition layer 184 can have a width smaller than, the same as, or larger than the width of the absorbent composite 140. Within the crotch region 116 of the absorbent article 110, the acquisition layer 184 can have a width smaller than, the same as, or larger than the width of the absorbent composite 140.

In an embodiment, the acquisition layer 184 can include natural fibers, synthetic fibers, superabsorbent material, woven material, nonwoven material, wet-laid fibrous webs, a substantially unbounded airlaid fibrous web, an operatively bonded, stabilized-airlaid fibrous web, or the like, as well as combinations thereof. In an embodiment, the acquisition layer 84 can be formed from a material that is substantially hydrophobic, such as a nonwoven web composed of polypropylene, polyethylene, polyester, and the like, and combinations thereof.

In various embodiments, the acquisition layer 184 can have fibers which can have a denier of greater than about 5. In various embodiments, the acquisition layer 184 can have fibers which can have a denier of less than about 5. In various embodiments, the fluid acquisition layer selected from metlblown-spunbond-meltblown fabric, spunbond fabric, meltblown fabric, coform fabric, carded web, bonded-carded web, bicomponent spunbond fabric, spunlace, tissue, and combinations thereof In an embodiment, the acquisition layer 84 can be a through-air bonded-carded web such as a 50 gsm through-air bonded-carded web composite having a homogenous blend of about 50% sheath/core bicomponent polyethylene/polypropylene fibers having a fiber diameter of 3 denier and about 50% sheath/core bicomponent polyethylene/polypropylene fibers having a fiber diameter of 1.5 denier. An example of such a composite is a composite having about 50% ES FiberVisions 3 denier ESC-233 bicomponent fibers and about 50% ES FiberVisions 1.5 denier ESC-215 bicomponent fibers, or equivalent composite, available from ES FiberVisions Corp., Duluth, Ga., U.S.A.

In an embodiment, the acquisition layer 184 can be a through-air bonded-carded web such as a 50 gsm through-air bonded-carded web composite having a homogenous blend of about 50% Rayon fibers having a fiber diameter of 3 denier and about 50% sheath/core bicomponent polyethylene/polypropylene fibers having a fiber diameter of 1.5 denier. An example of such a composite is a composite having about 50% Kelheim 3 denier Rayon Galaxy fibers and about 50% ES FiberVisions 1.5 denier ESC-215 bicomponent fibers, or equivalent composite, available from ES FiberVisions Corp., Duluth, Ga., U.S.A.

In an embodiment, the acquisition layer 184 can be a through-air bonded-carded web such as a 35 gsm through-air bonded-carded web composite having a homogenous mixture of about 35% sheath/core bicomponent polyethylene/polypropylene fibers having a fiber diameter of 6 denier, about 35% sheath/core bicomponent polyethylene/polypropylene fibers having a fiber diameter of 2 denier, and about 30% polyester fibers having a fiber diameter of 6 denier. An example of such a composite is a composite having about 35% Huvis 180-N (PE/PP 6d), about 35% Huvis N-215 (PE/PP 2d), and about 30% Huvis SD-10 PET 6d, or equivalent composite, available from SamBo Company, Ltd, Korea.

In an embodiment, the acquisition layer 184 can be a thermally bonded, stabilized-airlaid fibrous web (e.g. Concert product code DT200.100.D0001) which is available from Glatfelter, a business having offices located in York, Pa., U.S.A.

Containment Flaps:

In an embodiment, containment flaps, 150 and 152, can be secured to the body facing material 128 of the absorbent article 110 in a generally parallel, spaced relation with each other laterally inward of the leg openings 156 to provide a barrier against the flow of body exudates to the leg openings 156. In an embodiment, the containment flaps, 150 and 152, can extend longitudinally from the front waist region 112 of the absorbent article 110, through the crotch region 116 to the back waist region 114 of the absorbent article 110. The containment flaps, 150 and 152, can be bonded to the body facing material by a seam of adhesive 237 to define a fixed proximal end 238 of the containment flaps, 150 and 152.

The containment flaps, 150 and 152, can be constructed of a fibrous material which can be similar to the material forming the body facing material 128. Other conventional material, such as polymer films, can also be employed. Each containment flap, 150 and 152, can have a moveable distal end 236 which can include flap elastics, such as flap elastics 158 and 160, respectively. Suitable elastic materials for the flap elastic, 158 and 160, can include sheets, strands or ribbons of natural rubber, synthetic rubber, or thermoplastic elastomeric materials.

The flap elastics, 158 and 160, as illustrated, can have two strands of elastomeric material extending longitudinally along the distal ends 236 of the containment flaps, 150 and 152, in generally parallel, spaced relation with each other. The elastic strands can be within the containment flaps, 150 and 152, while in an elastically contractible condition such that contraction of the strands gathers and shortens the distal ends 236 of the containment flaps, 150 and 152. As a result, the elastic strands can bias the distal ends 236 of each containment flap, 150 and 152, toward a position spaced from the proximal end 238 of the containment flaps, 150 and 152, so that the containment flaps, 150 and 152, can extend away from the body facing material 128 in a generally upright orientation of the containment flaps, 150 and 152, especially in the crotch region 116 of the absorbent article 110, when the absorbent article 110 is fitted on the wearer. The distal end 236 of the containment flaps, 150 and 152, can be connected to the flap elastics, 158 and 160, by partially doubling the containment flap, 150 and 152, material back upon itself by an amount which can be sufficient to enclose the flap elastics, 158 and 160. It is to be understood, however, that the containment flaps, 150 and 152, can have any number of strands of elastomeric material and may also be omitted from the absorbent article 110 without departing from the scope of this disclosure.

Leg Elastics:

Leg elastic members, 166 and 168, can be secured between the outer and inner layers, 170 and 172, respectively, of the outer cover 126, such as by being bonded therebetween by laminate adhesive, generally adjacent the lateral outer edges of the inner layer 172 of the outer cover 126. Alternatively, the leg elastic members, 166 and 168, may be disposed between other layers of the absorbent article 110. A wide variety of elastic materials may be used for the leg elastic members, 166 and 168. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate.

Fastening System:

In an embodiment, the absorbent article 110 can include a fastener system. The fastener system can include one or more back fasteners 240 and one or more front fasteners 242. Portions of the fastener system may be included in the front waist region 112, back waist region 114, or both. The fastener system can be configured to secure the absorbent article 110 about the waist of the wearer and maintain the absorbent article 110 in place during use. In an embodiment, the back fasteners 240 can include one or more materials bonded together to form a composite ear as is known in the art. For example, the composite fastener may be composed of a stretch component 244, a nonwoven carrier or hook base 246, and a fastening component 248.

Waist Elastic Members:

In an embodiment, the absorbent article 110 can have waist elastic members, 162 and 164, which can be formed of any suitable elastic material. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members, 162 and 164, may be omitted from the absorbent article 110 without departing from the scope of this disclosure.

The absorbent structure 140 can be superposed over the inner layer 172 of the outer cover 126, extending laterally between the leg elastic members, 166 and 168, and can be bonded to the inner layer 172 of the outer cover 126, such as by being bonded thereto with adhesive. However, it is to be understood that the absorbent structure 140 may be in contact with, and not bonded with, the outer cover 126 and remain within the scope of this disclosure. In an embodiment, the outer cover 126 can be composed of a single layer and the absorbent composite 140 can be in contact with the singer layer of the outer cover 126. In an embodiment, a layer, such as but not limited to, a core wrap layer 178, can be positioned between the absorbent composite 140 and the outer cover 126.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent composite comprising:
a particulate superabsorbent material, wherein the absorbent composite comprises between about 20% and about 80% by weight of the particulate superabsorbent material;
a swellable absorbent fiber, wherein the absorbent composite comprises between about 20% and 80% by weight of the swellable absorbent fiber;
wherein the swellable absorbent fiber is substantially water-insoluble and water-swellable; and
wherein the swellable absorbent fiber exhibits a centrifuge retention capacity of between 5 and 20 grams per gram after four hours and reaches at least 66% of the centrifuge retention capacity between about 2 and about 50 seconds.

2. The absorbent composite of claim 1 wherein the swellable absorbent fiber reaches at least 66% of the centrifuge retention capacity between about 2 and about 20 seconds.

3. The absorbent composite of claim 1 wherein the swellable absorbent fiber has a diameter of between 10 and 50 microns.

4. The absorbent article of claim 1 wherein the absorbent core comprises at least 45% by weight of the absorbent fibers.

5. The absorbent article of claim 1 wherein the absorbent core comprises between 45% and 65% by weight of the absorbent fibers.

6. The absorbent article of claim 1 wherein the absorbent core comprises at least 35% by weight of the superabsorbent material.

7. The absorbent article of claim 1 wherein the absorbent core comprises about 35% to about 55% by weight of the superabsorbent material.

8. An absorbent article comprising:
  a topsheet;
  a backsheet; and
  an absorbent core disposed between the topsheet and the backsheet;
  wherein the absorbent core includes:
    a particulate superabsorbent material, wherein the absorbent composite comprises between about 20% and about 80% by weight of the particulate superabsorbent material;
    a swellable absorbent fiber, wherein the absorbent composite comprises between about 20% and 80% by weight of the swellable absorbent fiber;
    wherein the swellable absorbent fiber is substantially water-insoluble and water-swellable; and
    wherein the swellable absorbent fiber exhibits a centrifuge retention capacity of between 5 and 20 grams per gram after four hours and reaches at least 66% of the centrifuge retention capacity between about 2 and about 50 seconds.

9. The absorbent article of claim 8 wherein the swellable absorbent fiber reaches at least 66% of full capacity between about 2 and about 20 seconds.

10. The absorbent article of claim 8 wherein the swellable absorbent fiber has a diameter of between 10 and 50 microns.

11. The absorbent article of claim 8 wherein the absorbent core comprises at least 45% by weight of the absorbent fibers.

12. The absorbent article of claim 8 wherein the absorbent core comprises between 45% and 65% by weight of the absorbent fibers.

13. The absorbent article of claim 8 wherein the absorbent core comprises at least 35% by weight of the superabsorbent material.

14. The absorbent article of claim 8 wherein the absorbent core comprises about 35% to about 55% by weight of the superabsorbent material.

15. The absorbent article of claim 8 wherein the absorbent core further comprises fluff.

16. The absorbent article of claim 8 wherein the article is selected from personal care absorbent articles, health/medical absorbent articles, household/industrial absorbent articles and sports/construction absorbent articles.

17. An absorbent core comprising:
  a particulate superabsorbent material, wherein the absorbent composite comprises between about 20% and about 80% by weight of the particulate superabsorbent material;
  a swellable absorbent fiber;
  wherein a total core capacity is between about 200 g and 990 g of 0.9% saline;
  wherein the swellable absorbent fiber is substantially water-insoluble and water-swellable; and
  wherein the swellable absorbent fiber exhibits a centrifuge retention capacity of between 5 and 20 grams per gram after four hours and reaches at least 66% of the centrifuge retention capacity between about 2 and about 50 seconds.

18. The absorbent core of claim 17 wherein the swellable absorbent fiber reaches at least 66% of full capacity between about 2 and about 20 seconds.

19. The absorbent core of claim 17 wherein the swellable absorbent fiber has a diameter of between 10 and 50 microns.

20. The absorbent core of claim 17 wherein the absorbent core comprises at least 45% by weight of the absorbent fibers.

21. The absorbent core of claim 17 wherein the absorbent core comprises between 45% and 65% by weight of the absorbent fibers.

22. The absorbent core of claim 17 wherein the absorbent core comprises at least 35% by weight of the superabsorbent material.

23. The absorbent core of claim 17 wherein the absorbent core comprises about 35% to about 55% by weight of the superabsorbent material.

\* \* \* \* \*